(12) United States Patent
Chappuis

(10) Patent No.: US 6,894,236 B2
(45) Date of Patent: May 17, 2005

(54) UNIVERSAL SURGICAL POWER TOOL FOOT PEDAL APPARATUS

(75) Inventor: James L. Chappuis, 3170 Lakeridge Dr., Marietta, GA (US) 30067

(73) Assignee: James L. Chappuis, Marietta, GA (US)

( * ) Notice: Subject to any disclaimer, the term of this patent is extended or adjusted under 35 U.S.C. 154(b) by 135 days.

(21) Appl. No.: 10/154,383

(22) Filed: May 23, 2002

(65) Prior Publication Data

US 2003/0004497 A1 Jan. 2, 2003

Related U.S. Application Data

(60) Provisional application No. 60/293,674, filed on May 25, 2001.

(51) Int. Cl.$^7$ ................................................ H01H 3/02
(52) U.S. Cl. ................................... 200/86.5; 200/61.85
(58) Field of Search ............................ 200/86.5, 61.85, 200/51 R, 331, 332.1, 338; 5/600, 616; 433/101; 307/112–124; 606/19, 32, 27, 41, 166, 167

(56) References Cited

U.S. PATENT DOCUMENTS

| | | | | | |
|---|---|---|---|---|---|
| 4,172,217 A | * | 10/1979 | Miller | ........................ | 200/86.5 |
| 4,280,164 A | * | 7/1981 | Kozek | ........................ | 361/179 |
| 5,043,594 A | * | 8/1991 | Carballo | ........................ | 307/31 |
| 5,319,996 A | * | 6/1994 | Harris | ........................ | 74/560 |
| 5,554,894 A | * | 9/1996 | Sepielli | ........................ | 307/119 |
| 6,639,332 B2 | * | 10/2003 | Metzler et al. | ............. | 307/119 |

* cited by examiner

*Primary Examiner*—Elvin Enad
*Assistant Examiner*—Lisa Klaus
(74) *Attorney, Agent, or Firm*—Thomas, Kayden, Horstemeyer & Risley, LLP

(57) ABSTRACT

A frame for an operating room controller is disclosed. The frame can include a pedal platform; a platform extension extending from the pedal platform; and a primary track being fixed to the pedal extension opposing the pedal platform.

20 Claims, 4 Drawing Sheets

UNIVERSAL SURGICAL POWER TOOL FOOT PEDAL APPARATUS

CROSS-REFERENCE TO RELATED APPLICATION

This application claims priority to copending U.S. provisional application entitled, "Universal Surgical Power Tool Foot Pedal Apparatus," having Ser. No. 60/293,674, filed May 25, 2001, which is entirely incorporated herein by reference.

TECHNICAL FIELD

The present invention is generally related to tools and apparatuses implemented in medical procedures, such as surgery, and, more particularly, is related to a universal surgical power tool foot pedal apparatus.

BACKGROUND OF THE INVENTION

Many surgical procedures require the use of multiple surgical tools. Some of the tools are somewhat simple, such as non-powered blades, scalpels and scrapers, while other tools, such as burrs and saws, are powered by various power sources, such as, for example, electrically or pneumatically. Use of such power tools requires a surgeon using the tool to turn the power to the tool on and off as necessary to activate and deactivate the tool during a surgical procedure. However, the surgeon's hands are often not available for such tasks. As a result, the power supply to many of these tools can be controlled with a pedal located on the floor underneath a table on which the patient is positioned. The pedal is designed to be operated by the surgeon's foot. Typically the surgeon depresses the pedal to supply power to the tool and releases the pedal to discontinue the supply of power to the tool. The pedals are typically not fixed in any particular location on the floor and are free to move around the floor. As such, the pedals move around within and out of reach, or at least easy reach, of the surgeon.

During any given surgical procedure a doctor may use a combination of several non-powered and powered tools. The non-powered tools are typically laid out on a table, tray, or the like and handed to the surgeon as needed by other personnel present in the operating room, such as a surgical assistant, a nurse, or the like. The use of several power tools, however, often results in a plurality of pedals strewn about the operating room floor underneath the operating table. During the course of the surgical procedure, as a result of repeated use and switching from pedal to pedal, the pedals often become tangled together or moved to a location underneath the table where the surgeon has difficulty finding the pedal without looking down at the floor or asking an assistant for help. Additionally, with the pedals being easily moved about the floor, when the surgeon does locate a pedal, it can be difficult for the surgeon to determine which pedal the surgeon's foot is touching. As such, it can be difficult to ascertain which tool will be powered when a given pedal is depressed, without also looking down.

It is also common during surgical procedures for the surgeon to alternate between working on various sides of the operating table. However, traditional surgical power tools that are operable by a foot pedal generally have only one pedal. Therefore, it is necessary to move the pedal from one side of the table to the other side of the table as required during the procedure. Where multiple surgical power tools are used in one procedure, moving the pedals back and forth from one side of the table to the other further contributes to the tangling of the pedals as well as the difficulty in locating and identifying the pedals by touch.

Thus, a heretofore unaddressed need exists in the industry to address the aforementioned deficiencies and inadequacies.

SUMMARY

The present disclosure provides a surgical pedal apparatus. Briefly described, in architecture, one embodiment of the apparatus, among others, can be implemented as follows: a frame for an operating room controller, including a pedal platform, a platform extension extending from said pedal platform, and a primary track being fixed to said pedal extension opposing said pedal platform.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
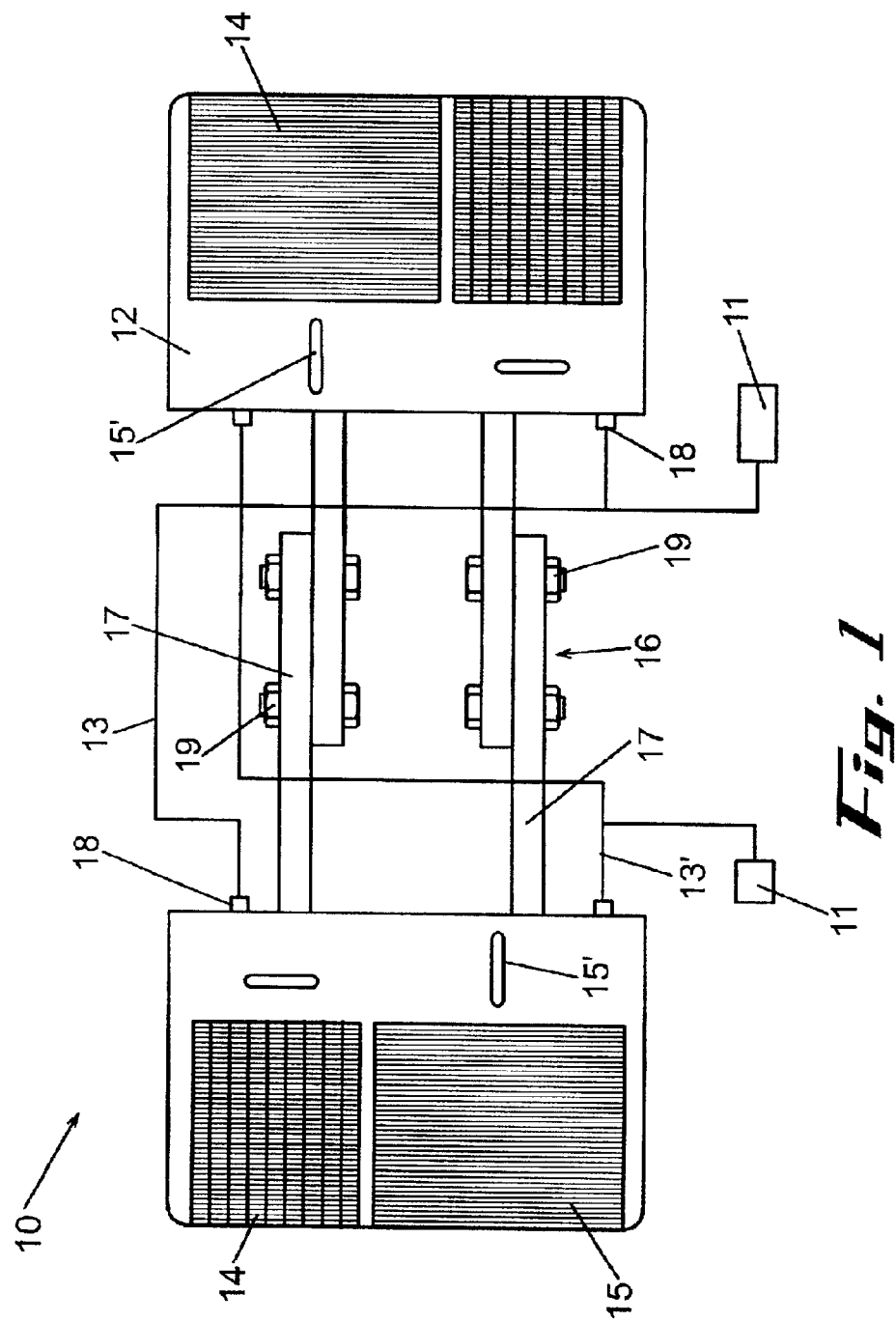
FIG. 1 illustrates a top plan view of an embodiment of the universal surgical power tool foot pedal apparatus of the present invention.

FIG. 1 illustrates an embodiment of the universal surgical power tool foot pedal apparatus 10 of the present invention. The foot pedal apparatus 10 includes at least one pedal platform 12 having at least one pedal 14 disposed thereon. The pedal platform 12 can have a plurality of pedals 14 disposed thereon.

It is preferred that each of the plurality of pedals 14 can be arranged and configured to facilitate user identification of the pedal 14 by touch alone. The pedals 14 can differ in size (shown), elevation from a top surface of the platform 12 (FIG. 2) or include a pedal identifier 15 disposed thereon, for example, but not limited to, a different textured pedal surface on each pedal 14. As illustrated in FIG. 1, the pedal identifier 15 can also serve as an anti-skid surface. Alternatively, the pedal platform 12 can include a means for user identification of the pedal 14 by touch disposed on the pedal platform 12 itself. The pedal identifier 15' is disposed on the pedal platform 12 substantially adjacent the pedal 14 with which the identifier 15' is associated. The pedal identifier 15' disposed on the platform 12 is a raised, or alternatively depressed, area. Each identifier 15' differs from other identifiers 15' in shape, size, orientation, or any suitable manner such that identification of an adjacent pedal can be readily ascertained. As illustrated, for example, each pedal identifier 15' differs in orientation from the other. Where the apparatus 10 comprises more than one pedal platform 12 (as described below) it is preferable that a pedal identifier 15, 15' be substantially similar for pedals on each pedal platform 12 capable of operating a common tool.

Figure 4:
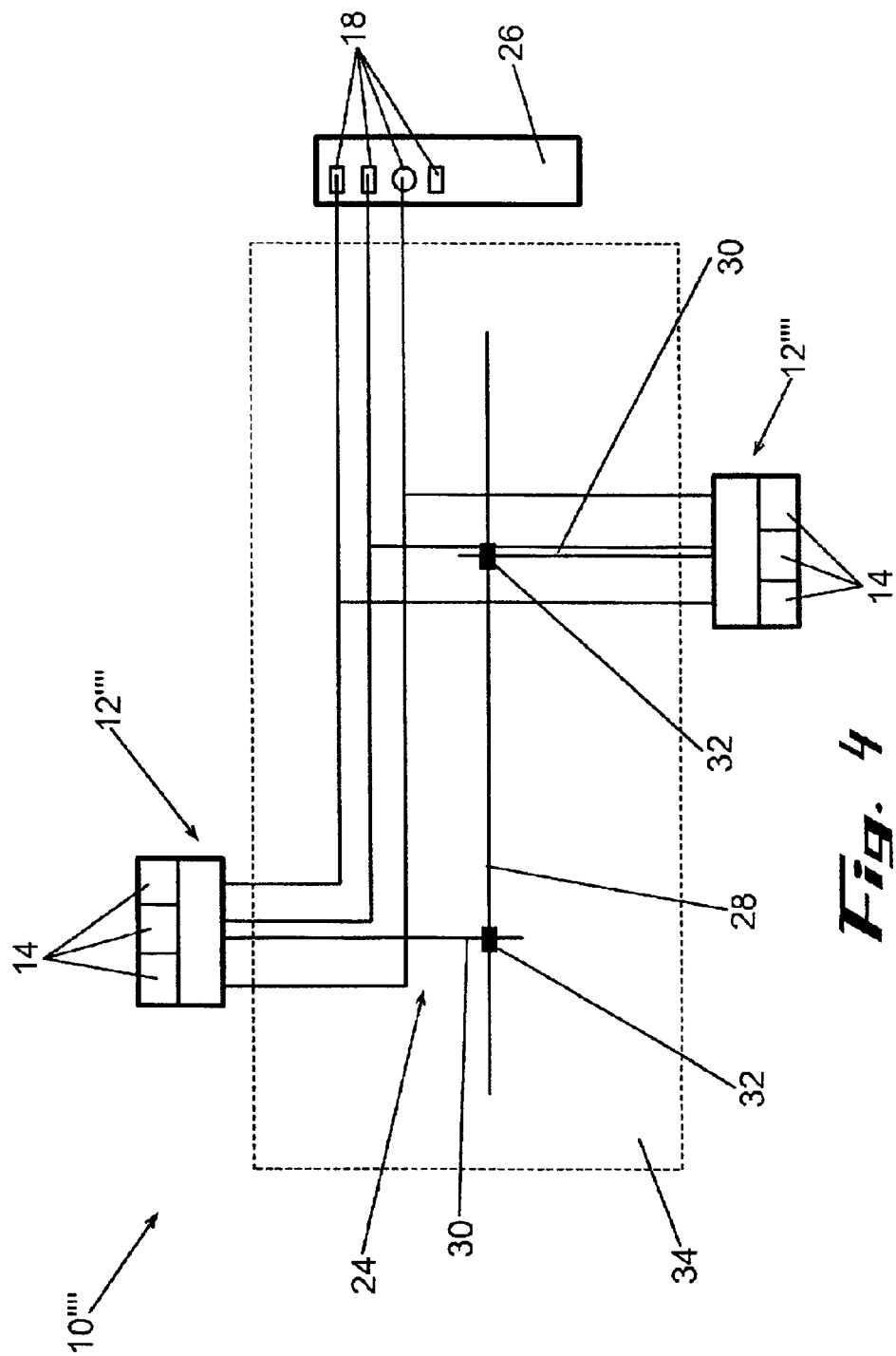
FIG. 4 is a top plan view of an embodiment of the universal surgical power tool foot pedal apparatus of the present invention.

The apparatus 10 further includes at least one plug receiver 18. The plug receiver 18 is disposed on the pedal platform 12. The plug receiver 18 is adapted to receive a power line 13 of a surgical tool 11 desired to be operated by a pedal 14. It is preferable that the pedal platform 12 includes a plurality of plug receivers 18 having various configurations being adapted to releasably receive power plugs of various configurations. It should be noted that the plug receiver 18 can also be separate from the pedal platforms 12, as illustrated in FIG. 4.

The surgical tool 11 itself can receive power directly from a power source, such as an electrical power source or a pneumatic power source. Alternatively, power can be transmitted through the apparatus 10 to a surgical tool 11. In this configuration the apparatus 10 receives power from a power source, such as an electrical power source or a pneumatic power source. Power is transmitted through the apparatus 10 to the surgical tool 11 and the surgical tool 11 is operated as desired.

The foot pedal apparatus 10 can include more than one pedal platform 12. Where the foot pedal apparatus 10 includes more than one pedal platform 12 a pedal 14 from each pedal platform 12 can be used to operate a common surgical tool 11. As an example, the broader of the two pedals illustrated in FIG. 1 could both be adapted to control the power feed to a burr. This arrangement facilitates the positioning of pedals 14 in more than one location underneath an operating table, or any desirable location on the operating room floor. The foot pedal apparatus 10 can also be adapted to control operating room environment. More specifically, a pedal 14 of the foot pedal apparatus 10 can be wired to control lights, temperature, music, etc. in an operating room.

The apparatus 10 can be positioned underneath an operating table on which a patient lies for surgery such that the pedal platforms 12 are disposed on opposing sides of an axis running the length of the operating table. The apparatus 10 can be positioned on the operating room floor or movably fixed to the operating room table. It is preferable that where the apparatus 10 is fixed to the operating table, such as to the underside, or any suitable area on the table, that the apparatus 10 is movable in various direction, such as laterally, upwardly, downwardly, etc. A pedal platform 12 can be disposed substantially adjacent each side of the operating table. Any given surgical tool can be operated from either side of the operating table without moving the pedals 14 from one side of the table to the other. Where a plurality of pedal platforms 12 comprise the foot pedal apparatus 10 the pedal platforms 12 can be connected together with a platform coupling 16.

The coupling 16 comprises a plurality of coupling arms 17 and coupling bolts 19. A pair of coupling arms 17 extends from each of pedal platforms 12. Each pair of coupling arms 17 are preferably arranged in a substantially parallel configuration. The coupling arms 17 of one pedal platform 12 are spaced apart with greater space therebetween than a distance between coupling arms 17 of the pedal platform 12 to be disposed opposite. The coupling arms 17 having greater space therebetween engage the opposing coupling arms 17 at the outside of each respective coupling arm 17 extending from the opposing pedal platform 12. Each opposing coupling arm 17 is fixed to the substantially corresponding coupling arm 17 of the opposing pair of coupling arms 17. The coupling arms 17 can be fixed by bolts 19, or any suitable means. It should be noted that any suitable means coupling the pedal platforms 12 together is within the spirit of the present invention.

Where more than one pedal platform 12 comprises the apparatus 10, it is preferable that a power line 13, 13' communicates with a pedal 14 on each pedal platform 12. In one embodiment, a power plug receiver 18 is disposed substantially adjacent each pedal 14 of each pedal platform 12 and represents a power plug receiver 18 associated with the substantially adjacent pedal 14. Power line 13 communicates with the pedal 14 smaller in size (also indicated by a pedal identifier 15' arranged horizontal the width of pedal 14) of each pedal platform 12. Power line 13' communicates with the pedal 14 larger in size (also indicated by a pedal identifier 15' arranged vertical the width of pedal 14) of each pedal platform 12.

Figure 2:
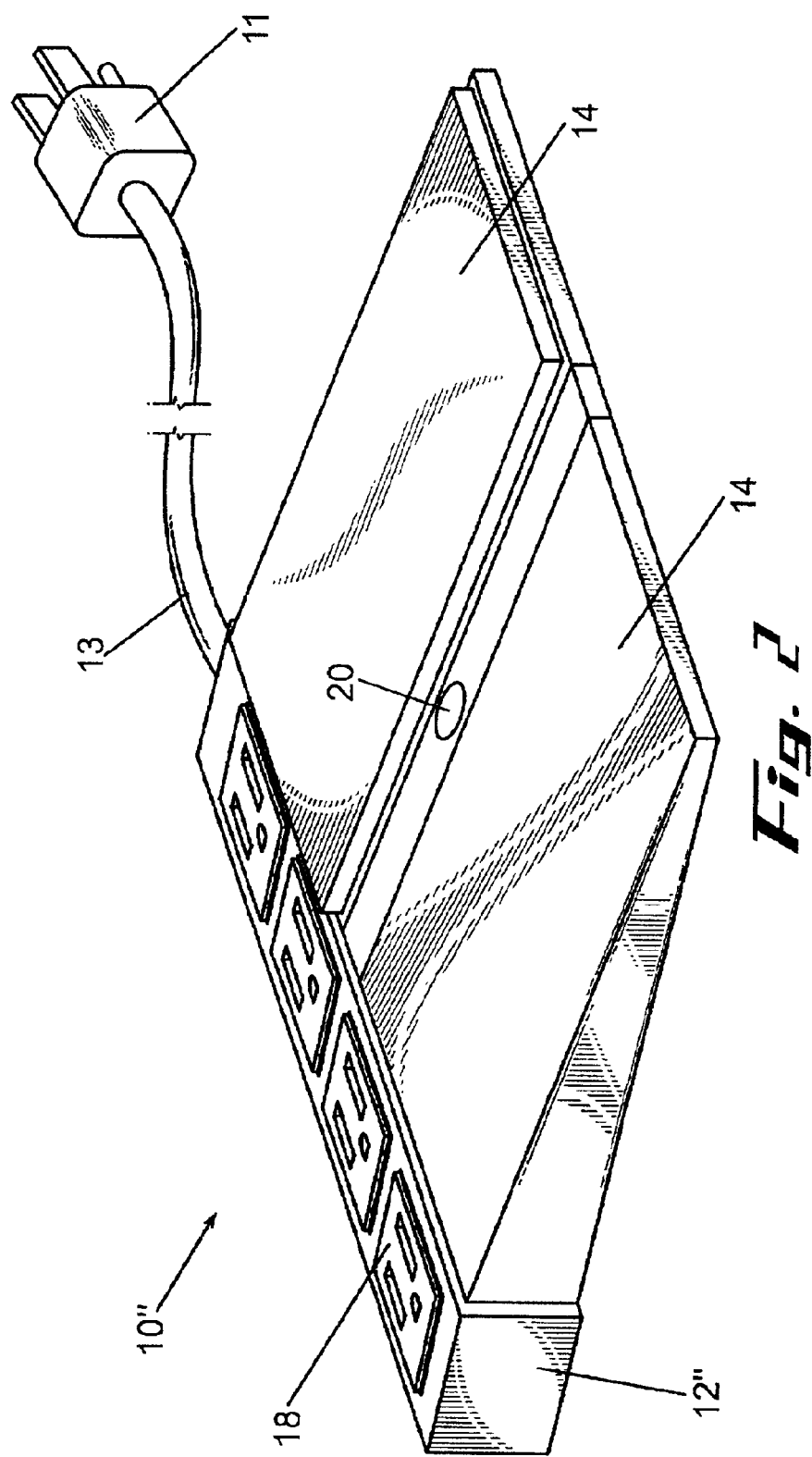
FIG. 2 illustrates a perspective view of an embodiment of the universal surgical power tool foot pedal apparatus of the present invention.

FIG. 2 illustrates a second embodiment of the foot pedal apparatus 10" of the present invention. The foot pedal apparatus 10" includes a pedal platform 12' having at least one pedal 14 disposed thereon. The pedal platform 12" and the foot pedal 14 both slant downward to facilitate ease of use and operation by the foot of the user. The pedal platform 12" can, however, comprise any suitable configuration. It is preferable that the pedal platform 12" includes more than one pedal 14 disposed thereon and that each of the plurality of pedals 14 is identifiable by touch. The pedals 14 can be distinguishable from each other by varying in size (shown in FIG. 1), by varying in elevation from a top surface of the pedal platform 12" (shown in FIG. 2), by a combination thereof, or any suitable means. This configuration can also include the tactile identifiers 15 and 15' illustrated in FIG. 1.

The pedal platform 12" can also include a selector switch 20. The selector switch 20 is adapted to alternate a pedal 14 between operating one surgical tool and operating another surgical tool, thereby allowing one pedal 14 to interchangeably operate more than one surgical tool. As illustrated in FIG. 2, a tool plug receiver 18 can be located on a top face of the pedal platform 12". Although a tool plug receiver 18 is illustrated in both FIGS. 1 and 2 as being disposed on said pedal platform 12", it should be understood that any means by which power can be communicated though a pedal 14 disposed on the pedal platform 12" to a surgical tool 11 such that the pedal 14 of the pedal platform 12" can be used to control the power supply to the tool 11 is within the spirit of the present invention. It should also be noted that although the configuration in FIG. 2 is illustrated comprising one pedal platform 12", this second embodiment can also include more than one pedal platform 12". The plurality of pedal platforms 12" can be fixed together and arranged and configured such that the pedals 14 of both pedal platforms 12" operate the same set of surgical tools.

More specifically, more than one pedal platform 12" can comprise the apparatus 10" of the present invention. A pair of pedal platforms 12" can be fixed together with a coupling 16, or the like. The pair of pedal platforms 12" are also preferably wired together such that a given surgical tool can be operated with a pedal 14 on each pedal platform 12".

Figure 3:
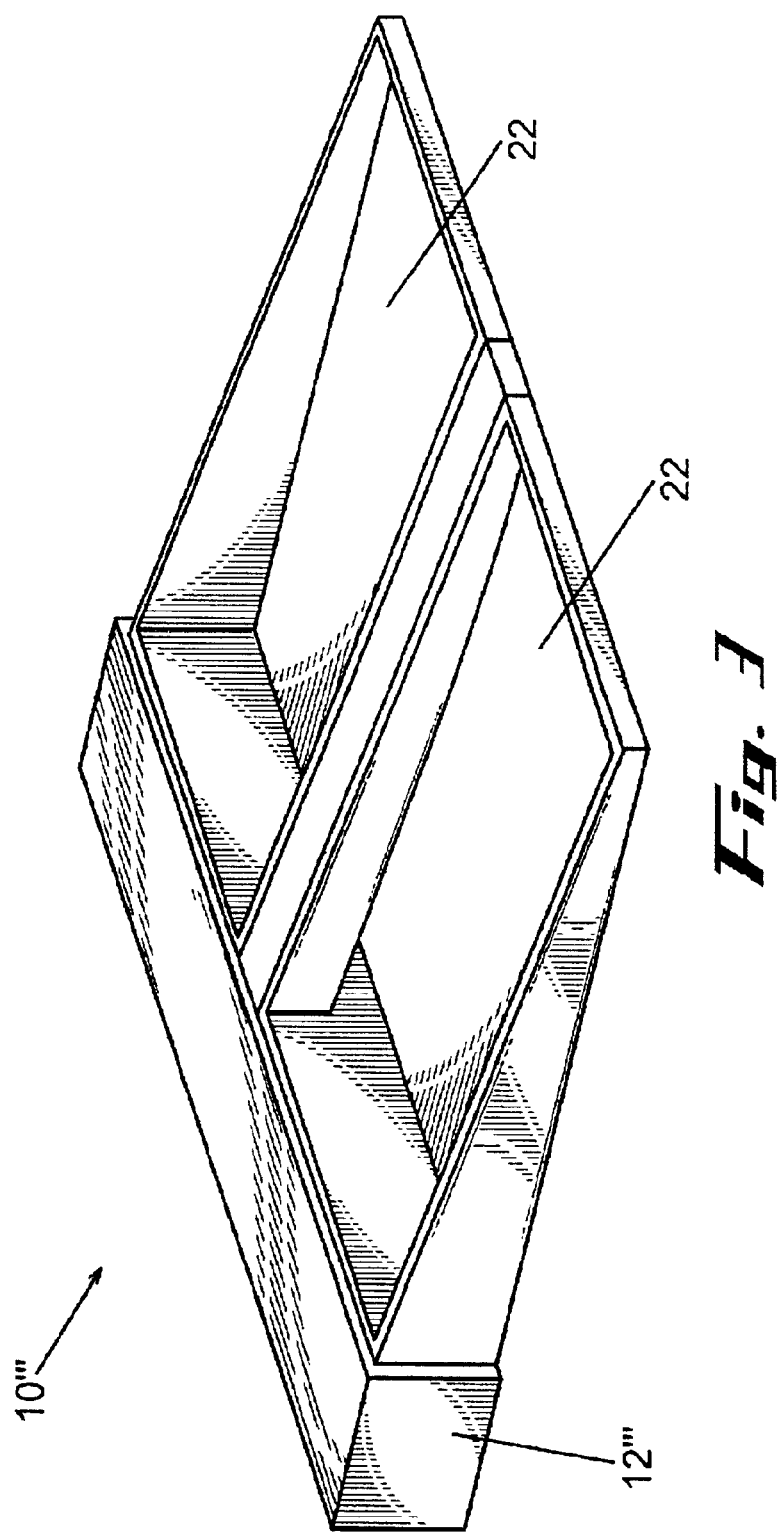
FIG. 3 illustrates a perspective view of an embodiment of the universal surgical power tool foot pedal apparatus of the present invention.

FIG. 3 illustrates another embodiment of the foot pedal apparatus 10'" of the present invention. The foot pedal apparatus 10''' includes at least one pedal platform 12''' comprising at least one pedal aperture 22. A preferred pedal aperture 22 is arranged and configured to releasably receive a pedal (not shown) to which a surgical tool 11 is attached. In this configuration the pedal platform 12''' acts as a rack or a holder for supporting and separating pedals for operating surgical tools that are marketed and sold with a pedal. It is preferable that the pedal platform 12''' includes a plurality of pedal apertures 22 in order to organize and separate a plurality of surgical power tool pedals. The pedal apertures 22 can be uniform in size and shape or configured of various sizes and shapes.

The foot pedal apparatus 10''' can also include a plurality of pedal platforms 12''', where each of the plurality of pedal platforms 12''' includes at least one pedal aperture 22. Each of the plurality of pedal platforms 12''' can also include a plurality of pedal apertures 22. Where more than one pedal platform 12''' is provided, it is preferable that a surgical tool 11 can have a pedal (not shown) disposed in a pedal aperture 22 of each of the plurality of pedal platforms 12'''. The plurality of pedal platforms 12''' can be fixed together. A splitter (not shown) as known to one skilled in the art, can be used to adapt a surgical tool having one pedal to having a pair of pedals such that one pedal can be disposed in one pedal platform 12'' and the other pedal can be disposed in the other pedal platform 12'''.

A pair of pedal platforms 12''' can be fixed together with a coupling 16, or any suitable means. It is also preferable that a pair of pedal platforms 12''' are wired together such that a surgical power tool can be operated by a pedal 14 on each pedal platform 12'''.

An identification means (such as an identification means 15' shown in FIG. 1) can be disposed on the pedal platform 22. It is preferable that a plurality of identification means (not shown), each at least slightly differing from the others, is disposed substantially adjacent each of the pedal apertures 22 disposed in the pedal platform 12'''. A preferred identification means (such as, for example but not limited to, a tactile identifier) facilitates a user distinguishing between pedals disposed in each of the pedal apertures 22 by touch.

FIG. 4 illustrates another embodiment of the foot pedal apparatus 10'''' of the present invention. The foot pedal apparatus 10'''' comprises at least one pedal platform 12'''', a frame 24 and a power supply 26. The pedal platform 12'''' comprises any of the pedal platforms 12, 12'', 12''' previously described herein. Furthermore, it should be noted that although two pedal platforms 12'''' are shown, any desired number of pedal platforms 12'''' can be included.

A frame 24 is preferably adjustable such that the location of each pedal platform 12'''' can be adjusted to a desired position and fixed in that desired position. The frame 24 comprises a primary track 28 and a pedal platform extension 30. The pedal platform extension 30 extends from each pedal platform 12'''' and intersects the primary track 28 at any suitable angle to the primary track 28. It should also be noted that although there are two pedal platform extensions 30 illustrated (one extending from each pedal platform 12'''' to the primary track 28) there can be any suitable number of pedal platform extensions 30. It is preferable that each pedal platform extension 30 is movably attached to the primary track 28 with a connector 32 that allows the position of the pedal platform 12'''' to be adjustable both along the primary track 28 as well as toward and away from the primary track 28. The connector 32 is preferably adapted to fix the pedal platform 12'''' in the desired position with respect to the primary track 28. A power supply 26 is positioned substantially adjacent the frame 24 and comprises a plurality of tool plug receivers 18. The power supply 26 provides power for electrical as well as pneumatic surgical tools. Frame 24 can be positioned, and optionally fixed, on the operating room floor or to a portion of the operating table, such as the underside or any suitable location. It is preferable that the where the frame 24 is fixed to the operating table that the pedal platforms 12'''' are additionally movable upwardly and downwardly. The pedal platform 12''' can also optionally be adapted to control the environmental conditions in the operating room, for example but not limited to, the lighting, temperature, music, etc.

In a method of use of the apparatus 10'''', the frame 24 is positioned beneath an operating table 34. The primary track 28 is positioned running substantially parallel the length of the operating table 34. The pedal platform extensions 30 extend substantially perpendicular to the length of the operating table 34 and away from the primary track 28 such that the pedal platform 12'''' is positioned along the side of the operating table 34. Where more than one pedal platform 12'''' is present, some of the pedal platforms 12'''' can be positioned toward one side of the operating table 34 and some of the pedal platforms 12 positioned toward the opposing side of the operating table 34. The pedal platforms 12'''' are arranged at any location with respect to the operating table 34 or at any location with respect to each other. It is further preferable that the pedal platforms 12'''' can be positioned as desired with respect to both the length and the width of the table 34 and fixed in the that desired position prior to surgery beginning.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention.

Therefore, having thus described the invention, at least the following is claimed:

1. A frame for an operating room controller, comprising:
   a pedal platform;
   a platform extension extending from said pedal platform; and
   a primary track being fixed to said pedal extension opposing said pedal platform.

2. The frame of claim 1, wherein said platform extension is movably fixed to said primary track.

3. The frame of claim 1, wherein said frame is fixed to a portion of floor in the operating room.

4. The frame of claim 1, wherein said frame is fixed to a portion of a table in an operating room, wherein said table is adapted to support a patient thereon.

5. The frame of claim 1, further comprising:
   a second pedal platform; and
   a second pedal platform extension being fixed to said primary track opposing said pedal platform.

6. The frame of claim 5, wherein said primary track is disposed between said pedal platform and said second pedal platform.

7. The frame for an operating room controller of claim 1, wherein said pedal platform further comprises:
   at least one pedal being adapted to move between a depressed position and a released position.

8. The frame for an operating room controller of claim 7, wherein said pedal is arranged and configured to substantially correspond to a human foot wherein said pedal can be moved between the depressed position and the released position with a human foot.

9. The frame for an operating room controller of claim 7, wherein said pedal platform further comprises a pedal identifier whereby a user can identify the pedal without viewing the pedal.

10. The frame for an operating room controller of claim 9, wherein said identifier comprises a tactile identifier whereby a user can identify said pedal by feel without viewing the pedal.

11. The frame of claim 7, wherein said pedal comprises a substantially ergonomic shape for a human foot.

12. The frame of claim 7, further comprising:
   a selector switch having multiple settings and being movable between said multiple settings;
   said pedal being arranged and configured to operate a plurality of surgical power tools,
   wherein said selector switch selects application of said pedal between operating one of said plurality of surgical power tools and another of said plurality of surgical power tools.

13. The frame for an operating room controller of claim 1, wherein said pedal platform comprises a plurality of pedals.

14. The frame of claim 13, wherein said pedal platform further comprises a plurality of identifiers, each of said plurality of identifiers being different from each of the other of said plurality of identifiers, whereby a user can identify which of said plurality of pedals the user is engaged without looking at said pedals.

15. The frame of claim 1, further comprising:
   an outlet in communication with said pedal platform, said outlet being adapted to releasably receive a power plug of a surgical power tool.

16. The frame of claim 15, wherein said outlet is arranged and configured to releasably receive plugs of various configurations.

17. The frame of claim 15, wherein said outlet is disposed on said pedal platform.

18. The frame of claim 15, wherein said outlet is disposed on an outlet platform, said outlet platform being in communication with said pedal platform.

19. The frame of claim 15, wherein said surgical power tool is pneumatically powered.

20. The frame of claim 15, wherein said surgical power tool is electrically powered.

* * * * *